(12) United States Patent
Szunyog

(10) Patent No.: US 9,603,570 B2
(45) Date of Patent: Mar. 28, 2017

(54) INTRAVASCULAR DEVICES, SYSTEMS, AND METHODS HAVING A SENSING ELEMENT EMBEDDED IN ADHESIVE

(71) Applicant: Volcano Corporation, San Diego, CA (US)

(72) Inventor: Chris Szunyog, Murrieta, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 14/850,578

(22) Filed: Sep. 10, 2015

(65) Prior Publication Data

US 2016/0073957 A1 Mar. 17, 2016

Related U.S. Application Data

(60) Provisional application No. 62/049,228, filed on Sep. 11, 2014.

(51) Int. Cl.
| | |
|---|---|
| *A61B 5/00* | (2006.01) |
| *A61B 5/0215* | (2006.01) |
| *A61B 8/12* | (2006.01) |
| *A61B 8/00* | (2006.01) |
| *A61M 25/00* | (2006.01) |

(Continued)

(52) U.S. Cl.
CPC .......... *A61B 5/6851* (2013.01); *A61B 5/0215* (2013.01); *A61B 8/12* (2013.01); *A61B 8/445* (2013.01); *A61B 5/026* (2013.01); *A61B 18/1492* (2013.01); *A61B 2018/00791* (2013.01); *A61B 2018/00863* (2013.01); *A61B 2090/064* (2016.02); *A61B 2562/12* (2013.01); *A61M 2025/0002* (2013.01); *A61M 2025/09066* (2013.01); *A61M 2025/09108* (2013.01); *A61M 2025/09166* (2013.01)

(58) Field of Classification Search
CPC ................ A61B 5/6851; A61M 25/09; A61M 2025/0002; A61M 2025/09083; A61M 2025/09166; A61M 2025/09175; A61M 2025/09183
See application file for complete search history.

(56) References Cited

U.S. PATENT DOCUMENTS

| | | |
|---|---|---|
| 5,125,137 A | 6/1992 | Corl et al. |
| 5,873,835 A | 2/1999 | Hastings et al. |

(Continued)

*Primary Examiner* — Max Hindenburg

(57) ABSTRACT

Intravascular devices, systems, and methods are disclosed. In some instances, the intravascular devices are guide wires that include a distal sensing element mounted partially within a housing and embedded and/or surrounded by a flexible adhesive. For example, in some implementations a sensing guide wire includes a flexible elongate member; a housing coupled to the flexible elongate member; a flexible element extending distally from the housing; and a sensing element coupled to the flexible elongate member such that a proximal portion of the sensing element is positioned within the housing and a distal portion of the sensing element is positioned within the flexible element. A flexible adhesive can embed or surround the distal portion of the sensing element positioned within the flexible element. Methods of making, manufacturing, and/or assembling such intravascular devices and associated systems are also provided.

20 Claims, 4 Drawing Sheets

(51) Int. Cl.
- *A61M 25/09* (2006.01)
- *A61B 5/026* (2006.01)
- *A61B 18/14* (2006.01)
- *A61B 18/00* (2006.01)
- *A61B 90/00* (2016.01)

(56) References Cited

U.S. PATENT DOCUMENTS

| | | |
|---|---|---|
| 6,106,476 A | 8/2000 | Corl |
| 6,551,250 B2 | 4/2003 | Khalil et al. |
| 8,936,559 B2 * | 1/2015 | Strommer ................ A61B 5/06 600/410 |
| 9,028,428 B2 * | 5/2015 | Maki ..................... A61M 25/09 600/585 |
| 9,044,202 B2 * | 6/2015 | Dekker ................. A61B 5/6851 |
| 9,126,021 B2 * | 9/2015 | Kanazawa ............ A61M 25/09 |
| 2014/0005543 A1 | 1/2014 | Burkett et al. |
| 2014/0180141 A1 | 6/2014 | Millett et al. |
| 2014/0187874 A1 | 7/2014 | Burkett et al. |
| 2014/0187980 A1 | 7/2014 | Burkett et al. |
| 2014/0187984 A1 | 7/2014 | Burkett et al. |
| 2015/0217090 A1 | 8/2015 | Burkett et al. |

* cited by examiner

INTRAVASCULAR DEVICES, SYSTEMS, AND METHODS HAVING A SENSING ELEMENT EMBEDDED IN ADHESIVE

CROSS REFERENCE TO RELATED APPLICATIONS

The present application claims priority to and the benefit of the U.S. Provisional Patent Application No. 62/049,228, filed Sep. 11, 2014, which is hereby incorporated by reference in its entirety.

TECHNICAL FIELD

The present disclosure relates to intravascular devices, systems, and methods. In some embodiments, the intravascular devices are guide wires that include a distal sensing element mounted partially within a housing and embedded and/or surrounded by a flexible adhesive.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel, visualize the inner lumen of the blood vessel, and/or otherwise obtain data related to the blood vessel. To date, guide wires containing pressure sensors, imaging elements, and/or other electronic, optical, or electro-optical components have suffered from reduced performance characteristics compared to standard guide wires that do not contain such components. For example, the handling performance of previous guide wires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guide wire.

Further, a problem with existing pressure and flow guide wires is that the coil(s) defining the distal tip of the device can be fragile and prone to unwanted bending or kinking. In that regard, the small diameter and high flexibility of the coil(s) limits the structural integrity that can be provided. Further, the rigid nature of the sensor housing adjacent to the coil(s) causes additional stress to be applied to the coil(s) during use, especially when traversing complex vasculature with many curves and turns. As a result, the handling and performance of the guide wires can be reduced because of the limitations of the coil(s).

Accordingly, there remains a need for improved intravascular devices, systems, and methods that include one or more electronic, optical, or electro-optical components.

SUMMARY

The present disclosure is directed to intravascular devices, systems, and methods that include a guide wire having a distal coil filled with a flexible adhesive.

For example, in some instances a sensing guide wire is provided that includes a flexible elongate member; a housing coupled to the flexible elongate member; a flexible element extending distally from the housing; and a sensing element coupled to the flexible elongate member such that a proximal portion of the sensing element is positioned within the housing and a distal portion of the sensing element is positioned within the flexible element. A flexible adhesive can surround the distal portion of the sensing element that is positioned within the flexible element. The sensing element can be a pressure sensor. The flexible element includes a coil in some instances. In that regard, the flexible adhesive fills a central lumen of the coil, but is spaced from an outer surface of the coil in some implementations.

In some instances, a method of forming a sensing guide wire is provided that includes coupling a housing to a distal portion of a flexible elongate member; coupling a flexible element to the distal portion of the flexible elongate member such that the flexible element extends distally from the housing; and coupling a sensing element to the distal portion of the flexible elongate member such that a proximal portion of the sensing element is positioned within the housing and a distal portion of the sensing element is positioned within the flexible element. The method can further include surrounding the distal portion of the sensing element with a flexible adhesive. In that regard, the step of surrounding the distal portion of the sensing element with the flexible adhesive can be performed before and/or after coupling the flexible element to the distal portion of the flexible elongate member. Further, the step of surrounding the distal portion of the sensing element with the flexible adhesive can include filling a central lumen of a coil with the flexible adhesive such that the flexible adhesive is spaced from an outer surface of the coil. The method can also include forming a solder joint within the flexible element adjacent to and distal of the flexible adhesive surrounding the distal portion of the sensing element within the flexible element.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
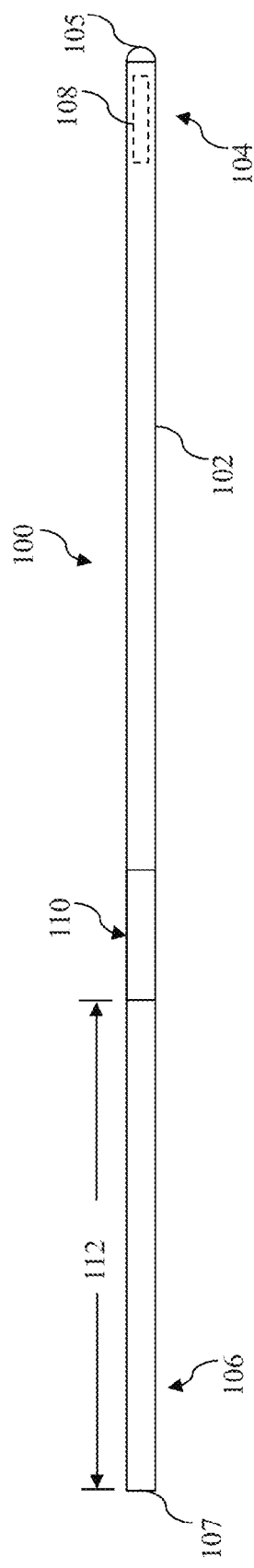
FIG. 1 is a diagrammatic, schematic side view of an intravascular device according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a flow sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm), approximately 0.018" (0.4572 mm), and approximately 0.035" (0.889 mm). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a portion of an intravascular device 100 according to an embodiment of the present disclosure. In that regard, the intravascular device 100 includes a flexible elongate member 102 having a distal portion 104 adjacent a distal tip 105 and a proximal portion 106 adjacent a proximal end 107. A component 108 is positioned within the distal portion 104 of the flexible elongate member 102 proximal of the distal tip 105. Generally, the component 108 is representative of one or more electronic, optical, or electro-optical components. In that regard, the component 108 is a pressure sensor, a flow sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the flexible elongate member 102. In that regard, the housing is a separate component secured to the flexible elongate member 102 in some instances. In other instances, the housing is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. In some embodiments the electrical conductors are embedded within a core of the flexible elongate member. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Similarly, in some embodiments the optical fibers are embedded within a core of the flexible elongate member. Further, in some embodiments the connector 110 provides both electrical and optical connections to both electrical conductor(s) and optical communication pathway(s) coupled to the component 108. In that regard, it should be noted that component 108 is comprised of a plurality of elements in some instances. The connector 110 is configured to provide a physical connection to another device, either directly or indirectly. In some instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. In some instances, at least one of the electrical conductors and/or optical pathways is embedded within the core of the flexible elongate member 102, as described in U.S. Provisional Patent Application No. 61/935,113, filed Feb. 3, 2014, now published as U.S. Patent Application Publication No. 2015/0217090 on Aug. 6, 2015, which is hereby incorporated by reference in its entirety. Generally, any number of electrical conductors, optical pathways, and/or combinations thereof can extend along the length of the flexible elongate member 102 between the connector 110 and the component 108, embedded in the core or not. In some instances, between one and ten electrical conductors and/or optical pathways extend along the length of the flexible elongate member 102 between the connector 110 and the component 108. The number of communication pathways and the number of electrical conductors and optical pathways extending along the length of the flexible elongate member 102 is determined by the desired functionality of the component 108 and the corresponding elements that define component 108 to provide such functionality.

Figure 2:
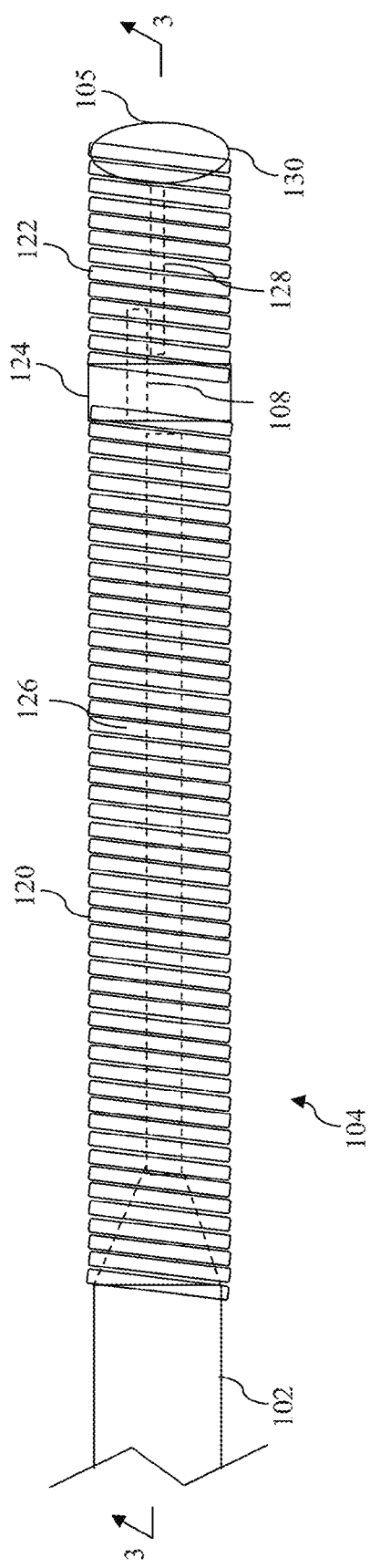
FIG. 2 is a diagrammatic, schematic side view of a distal portion of the intravascular device of FIG. 1 according to an embodiment of the present disclosure.
Figure 3:
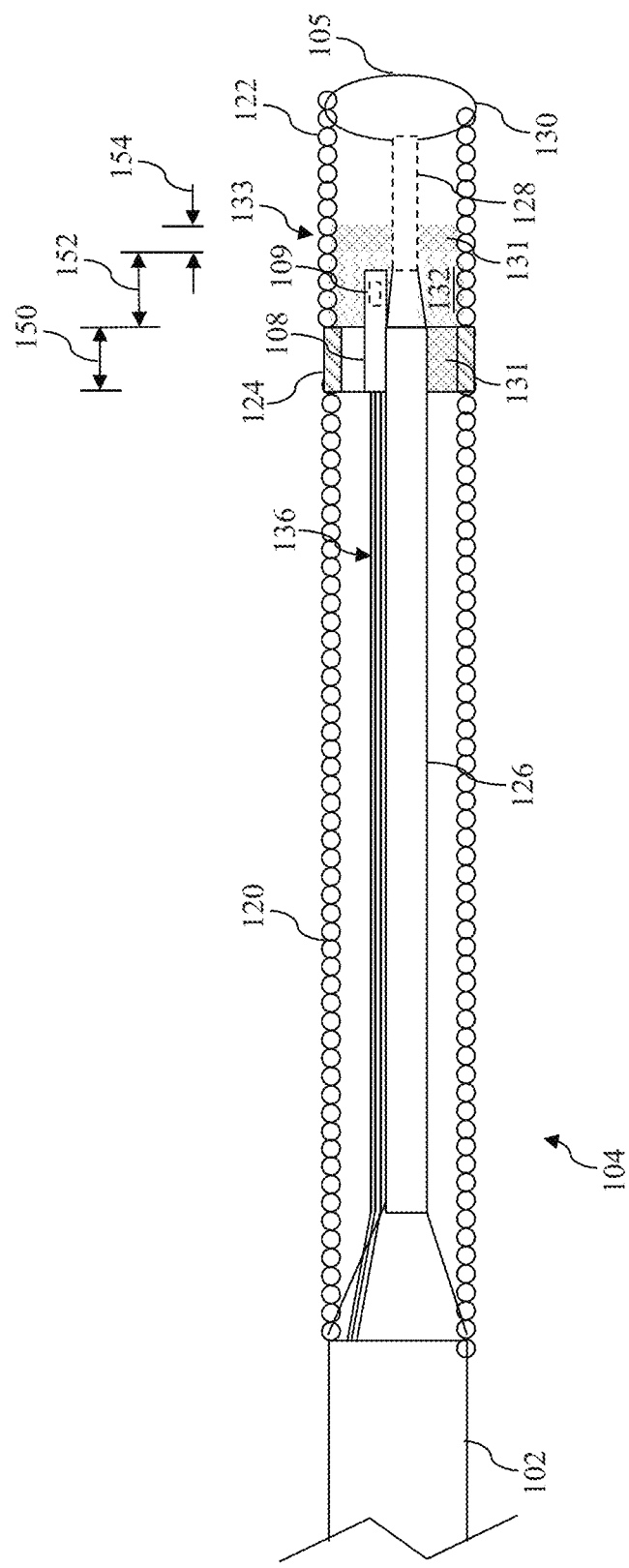
FIG. 3 is a cross-sectional side view of the distal portion of the intravascular device of FIGS. 1 and 2 taken along section line 3-3 of FIG. 2 according to an embodiment of the present disclosure.
Figure 4:
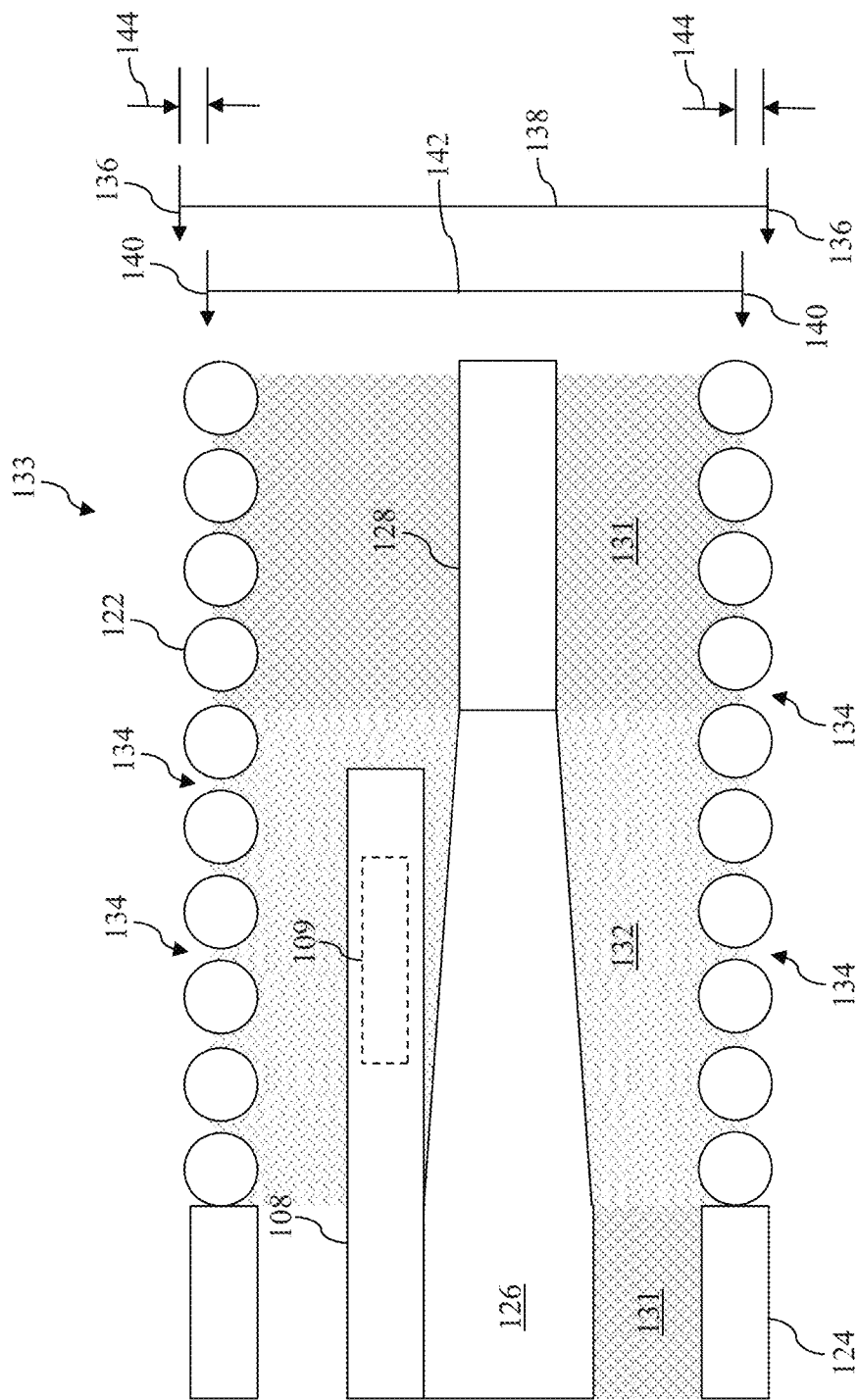
FIG. 4 is a magnified cross-sectional side view of a section of the distal portion of the intravascular device of FIGS. 1-3 according to an embodiment of the present disclosure.

Referring now to FIGS. 2-4, shown therein are aspects of the intravascular devices of the present disclosure that include a sensing element covered and/or surrounded by a flexible adhesive. In that regard, one of the major issues associated with existing functional guide wires is poor mechanical performance as compared to frontline guide wires. The use of an adhesive covered and/or surrounded sensing element, such as component 108 described above, within the distal portion of the intravascular device in accordance with the present disclosure has been found to significantly improve the mechanical performance of the guide wires by allowing a significant reduction and/or the elimination of the rigid housing for the sensing element.

Referring now to FIG. 2, shown therein is a diagrammatic, schematic side view of the distal portion 104 of the intravascular device 100 according to an embodiment of the present disclosure. As shown, the distal portion 104 includes a proximal flexible element 120 and a distal flexible element 122 on each side of a housing 124. As discussed below, in some instances the housing 124 is formed and/or coated with a radiopaque material. In that regard, the housing 124 is generally formed from a rigid material, such as a metal or rigid polymer. In some instances, the housing 124 is formed of stainless steel, which may be coated with another material to increase its radiopacity. Further, in the illustrated embodiment the housing 124 has a cylindrical shape, but other geometrical, non-geometrical, symmetrical, and non-symmetrical shapes can be utilized.

A core member 126 extends through the proximal flexible element 120. Similarly, a core member 128 extends through the distal flexible element 122. Generally, the core members 126, 128 are sized, shaped, and/or formed out of particular material(s) to create a desired mechanical performance for the distal portion 104 of the intravascular device 100. In that regard, the core members 126, 128 may be separate components joined together or a single, integral component. For example, in some instances a single, integrally formed core wire is shaped (e.g., by grinding, ablating, cutting, etc.) to define different sections corresponding to core members 126 and 128.

The proximal and distal flexible elements 120, 122 can be any suitable flexible element, including coils, polymer tubes, and/or coil-embedded polymer tubes. In the illustrated embodiment the proximal flexible element 120 and the distal flexible element 122 are coils. In some instances, all or a majority of the proximal flexible element 120 is filled with a flexible adhesive to improve the mechanical performance and durability of the intravascular device 100 as described in U.S. Provisional Patent Application No. 62/043,115, filed Aug. 28, 2014, which is hereby incorporated by reference in its entirety. Similarly, in some instances all or a majority of the distal flexible element 122 is filled with a flexible adhesive to improve the mechanical performance and durability of the intravascular device 100 as described in U.S. Provisional Patent Application No. 62/042,971, filed Aug. 28, 2014, which is hereby incorporated by reference in its entirety. Further, a solder ball 130 or other suitable element is secured to the distal end of the distal flexible element 122. As shown, the solder ball 130 defines the distal tip 105 of the intravascular device 100 with an atraumatic tip suitable for advancement through patient vessels, such as vasculature. In some embodiments, a flow sensor is positioned at the distal tip 105 instead of the solder ball 130.

The distal portion 104 of the intravascular device 100—as well as the proximal portion 106 and the flexible elongate member 102—may be formed using any suitable approach for use with the features described in the present disclosure. Accordingly, in some implementations the intravascular device 100 includes features similar to the distal, intermediate, and/or proximal sections described in one or more of U.S. Pat. Nos. 5,125,137, 5,873,835, 6,106,476, 6,551,250, U.S. patent application Ser. No. 13/931,052, filed Jun. 28, 2013, now published as U.S. Patent Application Publication No. 2014/0005543 on Jan. 2, 2014, U.S. patent application Ser. No. 14/135,117, filed Dec. 19, 2013, now published as U.S. Patent Application Publication No. 2014/0180141 on Jun. 26, 2014, U.S. patent application Ser. No. 14/137,364, filed Dec. 20, 2013, now published as U.S. Patent Application Publication No. 2014/0187980 on Jul. 3, 2014, U.S. patent application Ser. No. 14/139,543, filed Dec. 23, 2013, now published as U.S. Patent Application Publication No. 2014/0187984 on Jul. 3, 2014, U.S. patent application Ser. No. 14/143,304, filed Dec. 30, 2013, now published as U.S. Patent Application Publication No. 2014/0187874 on Jul. 3, 2014, and U.S. Provisional Patent Application No. 61/935,113, filed Feb. 3, 2014 now published as U.S. Patent Application Publication No. 2015/0217090 on Aug. 6, 2015, each of which is hereby incorporated by reference in its entirety.

Referring now to FIG. 3, shown therein is a cross-sectional side view of the distal portion 104 of the intravascular device 100 taken along section line 3-3 of FIG. 2 according to an embodiment of the present disclosure. As shown, a proximal portion of the component 108 is positioned within the housing 124, while a distal portion of the component is positioned within the distal flexible element 122. To that end, the electrical, optical, and/or electro-optical connections to the components 108 can be made within the housing 124 and, thereby, protected by the housing 124 during additional manufacturing steps, transportation, and/or use. For example, in the illustrated embodiment, a trifilar 136 is shown electrically connecting to the component 108 within the housing 124 and extending proximally toward the flexible elongate member 102. The distal and/or working portion of the component 108 is positioned outside of the housing 124 and within the distal flexible element 122. Because of this arrangement the size of the housing 124 can be reduced, thereby decreasing the corresponding rigidity caused by a having larger housing 124 and increasing the flexibility and handling performance of the intravascular device. Since the distal portion of the component is not positioned within the housing 124, care must be taken to ensure that the distal portion of the component 108 is protected yet accessible to its surroundings to perform its intended function(s).

Accordingly, in some implementations the distal portion of the component 108 is embedded and/or surrounded by a material 132. For example, in some implementations, the component 108 is a pressure sensor and the material 132 is configured to facilitate transfer of ambient pressure forces to a diaphragm or other sensing structure 109 of the pressure sensor. In addition, the material 132 can be configured to improve the mechanical integrity of the distal flexible element 122, while maintaining sufficient flexibility for use of the intravascular device in tortuous vessels. In some instances, the material 132 is a flexible adhesive such as Loctite 5248 having shore hardness of 25 A. Generally, the material 132 will be classified as a soft or extra soft material in the Shore scale, for example having a maximum durometer of Shore A 35. In the context of a coil distal flexible element 122, the flexible adhesive can secure the windings in place relative to one another, which helps protect the component 108 of the intravascular device 100 from damage during subsequent manufacturing steps, transport, and/or use.

The housing 124 can be secured to the core member 126 using any suitable techniques, including soldering, gluing, welding, etc. In some instances, the housing 124 is secured to the core member 126 with solder 131 as shown. Similarly, the distal flexible element 122 can be secured the core member 128 using any suitable techniques, including soldering, gluing, welding, etc., but in some instance is secured with solder 131. In some particular instances, a solder joint 133 is formed distal of the component 108 such that the housing 124 and/or the associated solder 131 used to secure the housing the core member 126 serves as a radiopaque marker proximal of the component 108, while the solder joint 133 serves as a radiopaque marker distal of the component 108. By tracking the position of the radiopaque markers defined by the housing 124 and solder 131 and knowing the relative distance of the component 108 to each of the radiopaque markers, the location of the component 108 during use can be established and utilized to improve diagnosis and/or treatment of the patient. Further, in some instances knowing the location of the component 108 during use facilitates co-registering the information/data obtained by the component 108 with other diagnostic information/images. The solder joint 133 can also serve as a distal boundary for the material 132 in which the component 108 is embedded in and/or surrounded by.

FIG. 3 illustrates that the housing 124 extends along the length of the intravascular device 100 a distance 150, the material 132 embedding and/or surrounding the distal portion of the component 108 extends along the length of the intravascular device a distance 152, and the solder joint 133 extends along the length of the intravascular device a distance 154. While the distances 150, 152, and 154 can take on virtually any combination of suitable lengths, in some particular embodiments the distance 150 is between about 1 mm and about 4 mm, the distance 152 is between about 1 mm and about 20 mm, and the distance 154 is between about 0.5 mm and about 2 mm. In some implementations, the distances 150 and 154 are equal or substantially equal. Further, in some instances the housing 124 and the solder joint 133 are equally spaced from an active element (e.g., diaphragm or sensing structure 109) of the component 108. Generally, the distances 150, 152, and 154 are selected to provide good flexibility and conformability to vessel tortuosity. Further, the resulting structures are positioned proximal to the tip to allow for tip shaping, if desired.

Referring now to FIG. 4, shown therein is a magnified cross-sectional side view of the distal portion 104 of the intravascular device 100 according to an embodiment of the present disclosure. As shown, the material 132 fills a central lumen of the distal flexible element 122 such that it surrounds a distal portion of the component 108. In some instances, the material 132 at least partially fills spaces 134 between adjacent windings of the distal flexible element 122. In that regard, in some instances the material 132 is introduced into the central lumen of the distal flexible element 122 through the spaces 134 (e.g., by wicking, injecting, dipping, spreading, manual application, and/or combinations thereof). In some instances, the material 132 is introduced into the central lumen of the distal flexible element 122 through an opening in one of the ends of the flexible element 122 and filled until the material at least partially fills the spaces 134. In that regard, the material 132 is spaced from the outer most surface(s) 136 of the distal flexible element 122 in some embodiments.

As shown, the outer most surfaces 136 of the distal flexible element 122 have a diameter 138. Generally, the diameter 138 is approximately equal to the maximum desired outer diameter of the intravascular device 100. Accordingly, in some particular implementations the diameter 138 is about 0.014", 0.018", or 0.035". The outer boundary 140 of the material 132 and/or the solder 131 has a diameter 142 that is smaller than the diameter 138 of the distal flexible element 122 such that the material is spaced from the outer most surface(s) 136 of the distal flexible element. In some instances, the diameter 142 is less than the diameter 138 by between about 0.0001" and about 0.0005" or other suitable range. Accordingly, in some instances, the diameter 142 is about 0.013", 0.017", or 0.034".

By spacing the material 132 and/or solder 131 from the outer most surface(s) 136 of the distal flexible element 122, the tactile response to a user associated with the distal flexible element 122 contacting anatomical structures is maintained. On the other hand, if too much of the material 132 and/or solder 131 covers the outer surface(s) of the distal flexible element 122, then a continuous surface of material 132 may be formed that can adversely affect the tactile response of the intravascular device 100 when in use.

In some instances, a method of forming or manufacturing a sensing guide wire in accordance with the present disclosure includes providing the requisite components and coupling them together in a manner to form the intravascular device 100. For example, in some instances a housing (such as housing 124) is coupled to a distal portion of a flexible elongate member (such as flexible elongate member 102) and a sensing element (such as component 108) positioned partially within the housing and partially within a flexible element (such as distal flexible element 122) extending distally from the housing. The flexible element is at least partially filled with a flexible material (such as a flexible adhesive) such that the flexible material embeds and/or surrounds a distal portion of the sensing element. The sensing element can be coupled to the housing and the flexible element, including being embedded and/or surrounded by the flexible material before or after coupling the housing and/or flexible element to the distal portion of the flexible elongate member. In that regard, the flexible material can be inserted into the flexible element using any suitable techniques, including wicking, injecting, dipping, spreading, manual application, and/or combinations thereof. In some instances where a coil is used as the flexible element, the flexible material fills the central lumen of the flexible element surrounding the sensing element until the flexible material extends at least partially within spacings between adjacent windings of the coil, but spaced from an outer surface of the coil. In that regard, the outer boundary of the adhesive can be spaced from the outer surface of the coil by a distance of 0.0005" (or about half the diameter of the distal coil wire diameter) or more. In some instances, the coil has an outer diameter of approximately 0.014", 0.018", or 0.035". In some instances, the distal tip assembly begins at the sensor and moves distally to the formation of the distal most tip to allow the flexible material to fill in around the sensor.

Guide wires of the present disclosure can be connected to an instrument, such as a computing device (e.g. a laptop, desktop, or tablet computer) or a physiology monitor, that converts the signals received by the sensors into pressure and velocity readings. The instrument can further calculate Coronary Flow Reserve (CFR) and Fractional Flow Reserve (FFR) and provide the readings and calculations to a user via a user interface. In some embodiments, a user interacts with a visual interface to view images associated with the data obtained by the intravascular devices of the present disclosure. Input from a user (e.g., parameters or a selection) are received by a processor in an electronic device. The selection can be rendered into a visible display.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A sensing guide wire, comprising:
   a flexible elongate member having a proximal portion and distal portion;
   a housing coupled to the distal portion of the flexible elongate member;
   a flexible element extending distally from the housing; and
   a sensing element coupled to the distal portion of the flexible elongate member such that a proximal portion of the sensing element is positioned within the housing and a distal portion of the sensing element is positioned within the flexible element.

2. The guide wire of claim 1, wherein a flexible adhesive surrounds the distal portion of the sensing element positioned within the flexible element.

3. The guide wire of claim 2, wherein the sensing element is a pressure sensor.

4. The guide wire of claim 2, wherein the flexible element includes a coil.

5. The guide wire of claim 4, wherein the flexible adhesive has a cured hardness less than Shore A 35.

6. The guide wire of claim 4, wherein the flexible adhesive fills a central lumen of the coil, but is spaced from an outer surface of the coil.

7. The guide wire of claim 6, wherein the flexible adhesive is spaced from the outer surface of the coil by a distance of at least 0.0005".

8. The guide wire of claim 1, further comprising a solder joint positioned within the flexible element adjacent to and proximal of the flexible adhesive surrounding the distal portion of the sensing element within the flexible element.

9. The guide wire of claim 8, wherein the housing is firmed of a radiopaque material.

10. The guide wire of claim 8, wherein the housing is soldered to a core member.

11. A sensing guide wire, comprising:
- a flexible elongate member having a proximal portion and distal portion;
- a housing coupled to the distal portion of the flexible elongate member;
- a coil extending distally from the housing; and
- a sensing element coupled to the housing such that a proximal portion of the sensing element is positioned within the housing and a distal portion of the sensing element is positioned within the coil.

12. The guide wire of claim 11, further comprising a flexible adhesive surrounding the distal portion of the sensing element positioned within the coil.

13. The guide wire of claim 12, wherein the flexible adhesive has a cured hardness less than Shore A 35.

14. The guide wire of claim 12, wherein the flexible adhesive fills a central lumen of the coil, but is spaced from an outer surface of the coil.

15. The guide wire of claim 11, wherein the sensing element includes a pressure sensor.

16. The guide wire of claim 11, further comprising: a flexible element coupled to the flexible elongate member proximal of the housing.

17. The guide wire of claim 11, wherein the flexible element comprises at least one of a coil, a polymer tube, or a coil-embedded polymer tube.

18. The guide wire of claim 11, wherein the housing is formed of a radiopaque material.

19. The guide wire of claim 11, wherein the sensing element includes a flow sensor.

20. The guide wire of claim 11, wherein the sensing element includes a temperature sensor.

* * * * *